(12) United States Patent
Lou et al.

(10) Patent No.: US 11,708,576 B2
(45) Date of Patent: Jul. 25, 2023

(54) **RECOMBINANT *ESCHERICHIA COLI* EXPRESSING FUSION PROTEIN OF FORMAMIDASE AND PHOSPHITE DEHYDROGENASE AND CONSTRUCTION METHOD AND USE THEREOF**

(71) Applicant: SOUTH CHINA UNIVERSITY OF TECHNOLOGY, Guangdong (CN)

(72) Inventors: Wenyong Lou, Guangdong (CN); Xiaoyang Ou, Guangdong (CN); Minhua Zong, Guangdong (CN); Jiaxin Gao, Guangdong (CN); Fei Peng, Guangdong (CN); Pei Xu, Guangdong (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 98 days.

(21) Appl. No.: 16/627,760

(22) PCT Filed: Oct. 31, 2018

(86) PCT No.: PCT/CN2018/113237
§ 371 (c)(1),
(2) Date: Dec. 31, 2019

(87) PCT Pub. No.: WO2019/100919
PCT Pub. Date: May 31, 2019

(65) Prior Publication Data
US 2021/0163958 A1 Jun. 3, 2021

(30) Foreign Application Priority Data
Nov. 22, 2017 (CN) .......................... 2017111766728

(51) Int. Cl.
| | |
|---|---|
| *C12N 15/62* | (2006.01) |
| *C12N 15/70* | (2006.01) |
| *C12N 9/80* | (2006.01) |
| *C12N 9/02* | (2006.01) |
| *C12N 15/66* | (2006.01) |
| *C12Q 1/686* | (2018.01) |

(52) U.S. Cl.
CPC ............ *C12N 15/70* (2013.01); *C12N 15/66* (2013.01); *C12Q 1/686* (2013.01); *C12Y 120/01001* (2013.01); *C12Y 305/01049* (2013.01)

(58) Field of Classification Search
None
See application file for complete search history.

(56) References Cited

FOREIGN PATENT DOCUMENTS

| | | |
|---|---|---|
| CN | 105658801 | 6/2016 |
| CN | 107299072 | 10/2017 |
| CN | 107760642 | 3/2018 |
| CN | 108315288 | 7/2018 |

OTHER PUBLICATIONS

Registry of Standard Biological Parts, Part:BBa_K2325103, Oct. 16, 2017, designed by Xiaojia Liu, 3 pages (Year: 2017).*
"International Search Report (Form PCT/ISA/210) of PCT/CN2018/113237", dated Jan. 24, 2019, with English translation thereof, pp. 1-6.

* cited by examiner

*Primary Examiner* — David Steadman
(74) *Attorney, Agent, or Firm* — JCIPRNET

(57) ABSTRACT

The invention relates to a recombinant *Escherichia coli* expressing a fusion protein of formamidase and phosphite dehydrogenase, a construction method and use thereof. The invention includes adopting engineered *E. coli* DH5α as a host, amplifying a cloned formamidase gene and a cloned phosphite dehydrogenase gene into a fusion gene, ligating the fusion gene to a multiple cloning site of a vector, transforming the obtained recombinant plasmid into the *E. coli* DH5α, extracting the plasmid and transforming into an expression strain, and performing induction culture to obtain a recombinant *E. coli*. The recombinant *E. coli* can express a fusion protein of formamidase and phosphite dehydrogenase.

8 Claims, 2 Drawing Sheets
Specification includes a Sequence Listing.

RECOMBINANT *ESCHERICHIA COLI* EXPRESSING FUSION PROTEIN OF FORMAMIDASE AND PHOSPHITE DEHYDROGENASE AND CONSTRUCTION METHOD AND USE THEREOF

CROSS-REFERENCE TO RELATED APPLICATION

This application is a 371 of international application of PCT application serial no. PCT/CN2018/113237, filed on Oct. 31, 2018, which claims the priority benefit of China application no. 201711176672.8, filed on Nov. 22, 2017. The entirety of each of the above mentioned patent applications is hereby incorporated by reference herein and made a part of this specification.

BACKGROUND

Technical Field

The present invention relates to the field of genetic engineering, and more particularly, to a recombinant *Escherichia coli* expressing a fusion protein of formamidase and phosphite dehydrogenase, a construction method and use thereof.

Description of Related Art

*Escherichia coli* (*E. coli*) is one of the most widely used hosts at present, because the genome of *E. coli* is thoroughly researched, and *E. coli* has a fast multiplication speed and a short fermentation period. Therefore, the *E. coli* receives close concern and attention from entrepreneurs in the fermentation industry. However, in a fermentation process of *E. coli*, the problem of microbial contamination is still the most concerned problem for enterprises. In the case of microbial contamination, not only economic losses, and wastes of raw material and time are caused, but also a difficulty is added to waste disposal. Therefore, finding a way to solve the problem that the *E. coli* is contaminated by miscellaneous bacteria in a fermentation process is of great significance to promote the profit growth of enterprises and to the development of society.

At present, the research on microbial contamination mostly focuses on aspects such as sources (pathways) and related bacterium shapes of miscellaneous bacteria in *E. coli* fermentation, the influence of microbial contamination on fermentation at different fermentation stages and control measures, the analysis and control from the perspective of equipment, etc. In order to reduce the microbial contamination, enterprises generally focus on improving equipment requirements and technical level of operators. However, microbial contamination also occurs frequently in the fermentation process due to a complex surrounding environment and a hidden part of fermentation equipment.

In view of the above phenomenon of microbial contamination in a fermentation process of *E. coli*, researches are carried out focusing on the intake of a substrate spectrum of a nutrient substance, to modify a nutrient metabolic pathway of *E. coli*, so that the modified *E. coli* strain can express a fusion protein of formamidase and phosphite dehydrogenase. The fusion protein can decompose formamide to form ammonia as a nitrogen source, and oxidize phosphite to phosphate as a phosphorus source. By changing pathways of the nitrogen source and the phosphorus source, the modified *E. coli* strain can normally grow in a specific MOPS medium, while miscellaneous microorganisms not possessing the two metabolic pathways simultaneously will be "starved to death" due to the lack of the nitrogen source or the phosphorus source as sources of nutrient substances. On one hand, the recombinant *E. coli* can express a fusion protein using formamide and phosphite; and on the other hand, the recombinant *E. coli* can also express exogenous genes, including antibodies and other valuable enzyme preparations. Meanwhile, in order to verify an ability of the constructed engineered *E. coli* to synthesize the exogenous genes, a green fluorescent protein gene is also transformed into the engineered *E. coli* for co-expression.

SUMMARY

An objective of the present invention is, against the deficiency of the technology, to provide a recombinant *E. coli* expressing a fusion protein of formamidase and phosphite dehydrogenase, which is specifically capable of efficiently expressing a fusion protein of formamidase and oxidized phosphite dehydrogenase. The recombinant *E. coli* expresses a fusion protein gene for-Linker-ptx of formamidase gene and phosphite dehydrogenase gene to generate the fusion protein of formamidase and phosphite dehydrogenase, the fusion protein can simultaneously decompose formamide to form $NH_4^+$ and oxidize phosphite phosphate to phosphate, thereby providing a nitrogen source and a phosphorus source necessary for the growth and multiplication of the recombinant *E. coli*, while other microorganisms not possessing the two metabolic pathways simultaneously will be "starved to death" due to the lack of the metabolic pathways of the nitrogen source and the phosphorus source.

An objective of the present invention is further to provide a construction method of the recombinant *E. coli* expressing the fusion protein of formamidase and phosphite dehydrogenase. The construction method includes adopting *E. coli* DH5α as a host, amplifying a formamidase gene for-Linker from *Paenibacillus pasadenensis*. CS0611 which contains a linker sequence and a phosphite dehydrogenase gene ptx from *Klebsiella pneumonia*. OU7, assembling the two genes as a fusion gene for-Linker-ptx by an overlapping PCR technology, ligating the fusion gene to a multiple cloning site of a vector pGEX-2T, and transforming the obtained recombinant plasmid pGEX-for-Linker-ptx into the *E. coli* DH5α; and after successful verification, extracting the plasmid pGEX-for-Linker-ptx and transforming into an expression strain of *E. coli* BL21(DE3) to obtain a recombinant expression strain of *E. coli* BL21 (DE3)(pGEX-for-Linker-ptx), and continuing induction culture in a MOPS medium containing formamide and phosphite.

The formamidase gene for and the phosphite dehydrogenase gene ptx that are obtained by amplification are ligated by linker sequence, so that the two enzyme genes are fused and expressed to exert an enzyme catalytic function, thereby realizing normal growth and multiplication of the recombinant *E. coli* in the MOPS medium containing formamide and phosphite, and making the recombinant *E. coli* express its function.

An objective of the present invention is further to provide use of the recombinant *E. coli* expressing a fusion protein of formamidase and phosphite dehydrogenase.

The objectives of the present invention are achieved by the following technical solutions.

A construction method of an *E. coli* expressing a fusion protein of formamidase and phosphite dehydrogenase includes steps as follows:

(1) designing primers and amplifying a formamidase gene containing a linker sequence by PCR (the linker sequence at the 3'-end):

wherein a forward primer is A1 (5'-CGC<u>*GGATCC*</u>GATGAACGGACTGGGCGGCTTGAAC-3') of SEQ ID NO: 4, in which an underlined and italic part <u>GGATCC</u> is a restriction enzyme cutting site of BamH I; and a reverse primer is A2 (5'-CGACCCACCACCGCCCGAGCCACCGCCACCTCGC-GCCGCGCCTCCCTTCGC-3') of SEQ ID NO: 5, in which an underlined part <u>CGACCCACCACCGCCCGAGCCACCGCCACC</u> is the linker sequence of SEQ ID NO: 10;

using a genome of Paenibacillus pasadenensis. CS0611 as a template to clone a formamidase gene sequence for-Linker of 1041 bp containing the linker sequence; ligating the cloned gene sequence for-Linker into a vector pMD-19T Simple, and then transforming the recombinant vector into E. coli DH5α to obtain a recombinant E. coli DH5α(pMD-19T Simple-for-Linker) containing the recombinant vector pMD-19T Simple for-Linker; and then amplifying a for-Linker fragment with A1 and B1 (5'-TATAACGAGTTTCGGCAGCAT<u>CGACCCACCACCGCCCGAGCCA</u>-3') of SEQ ID NO: 6;

(2) designing primers and amplifying a phosphite dehydrogenase gene by PCR:

wherein, a forward primer is B2 (5'-<u>TGGCTCGGGCGGTGGTGGGTCG</u>ATGCTGCCGAAA-CTCGTTATA-3') of SEQ ID NO: 7, in which an underlined part <u>TGGCTCGGGCGGTGGTGGGTCG</u> is partial DNA of the linker of SEQ ID NO: 11; and a reverse primer is B3 (5'-CCG<u>GAATTC</u>CGACATGCGGCAGGCTCGGCC-TTGGGC-3') of SEQ ID NO: 8, in which an underlined and italic part <u>GAATTC</u> is a restriction enzyme cutting site of EcoR I;

using a genome of Klebsiella pneumonia. OU7 as a template to clone a phosphite dehydrogenase gene sequence ptx of 1008 bp to obtain a ptx DNA fragment;

(3) overlapping PCR amplification to obtain a fusion gene for-Linker-ptx:

using the for-Linker fragment and the ptx fragment that are obtained by amplification in the step (1) and the step (2) respectively as templates, and using the primer A1 and the primer B3 as the forward primer and the reverse primer respectively, amplifying to obtain the fusion gene for-Linker-ptx of the formamidase gene and the phosphite dehydrogenase gene; and performing double digestion on the fusion gene for-Linker-ptx with BamH I and EcoR I, ligating the fusion gene to a pGEX-2T expression plasmid digested with the same enzyme and transforming the recombinant plasmid into *E. coli* DH5α to obtain a positive clone *E. coli* DH5α(pGEX-for-Linker-ptx);

(4) transforming the recombinant plasmid into a recombinant expression strain:

extracting a recombinant plasmid pGEX-for-Linker-ptx from the recombinant *E. coli* DH5α(pGEX-for-Linker-ptx), and transforming the recombinant plasmid pGEX-for-Linker-ptx into an expression strain *E. coli* BL21(DE3) to obtain a recombinant expression strain *E. coli* BL21(DE3) (pGEX-for-Linker-ptx);

(5) performing induction culture on the recombinant *E. coli:* inoculating the obtained recombinant expression strain *E. coli* BL21(DE3)(pGEX-for-Linker-ptx) into a LB medium to perform induction culture, then collecting bacteria and adding the collected strain to a MOPS medium containing formamide and phosphite and continuing to culture to obtain the recombinant *E. coli.*

Further, in the step (1), the formamidase gene sequence containing the linker sequence from the strain of *Paenibacillus pasadenensis*. CS0611 is shown in SEQ ID NO: 1, which has a fragment length of 1041 bp, contains the linker sequence (GGTGGCGGTGGCTCGGGCGGTGGTGGGTCG) of SEQ ID NO: 9, and encodes 347 amino acids. and encodes 347 amino acids.

Further, in the step (1), the strain of *Paenibacillus pasadenensis*. CS0611 was preserved in China Center for Type Culture Collection on Oct. 8, 2014 with a preservation number of CCTCC NO: M2014458.

Further, in the step (1), conditions for the PCR amplification are as follows: reacting at 94° C. for 5 minutes; reacting at 98° C. for 10 seconds, reacting at 55° C. for 5 seconds and reacting at 72° C. for 70 seconds, and repeating the reactions for 30 times; then reacting at 72° C. for 7 minutes; and finally, cooling to 16° C.

Further, in the step (2), the phosphite dehydrogenase gene sequence from the strain of *Klebsiella pneumonia*. OU7 is shown in SEQ2, which has a fragment length of 1008 bp and encodes 336 amino acids.

Further, in the step (2), the strain if *Klebsiella pneumonia*. OU7 was preserved in China Center for Type Culture Collection on Aug. 24, 2017 with a preservation number of CCTCC NO: M 2017449.

Further, in the step (2), conditions for the PCR amplification are as follows: reacting at 94° C. for 5 minutes; reacting at 98° C. for 10 seconds, reacting at 55° C. for 5 seconds and reacting at 72° C. for 70 seconds, and repeating the reactions for 30 times; then reacting at 72° C. for 7 minutes; and finally, cooling to 16° C.

Further, in the step (3), the gene sequence of the fusion gene for-Linker-ptx is shown in SEQ ID NO: 3, which has a fragment length of 2049 bp, with the formamidase gene located at a 5'-end and the phosphite dehydrogenase gene located at a 3'-end, and a formamidase gene fragment is ligated to a phosphite dehydrogenase gene fragment by the linker sequence (GGTGGCGGTGGCTCGGGCGGTGGTGGGTCG) of SEQ ID NO: 9 with a fragment length of 30 bp.

The linker sequence is located at the 3'-end of the formamidase gene, so that 10 hydrophobic amino acids act as a chain bridge between the formamidase and phosphite dehydrogenase, so that these two proteins cannot influence each other when forming an active three-dimensional spatial structure.

Further, in the step (3), conditions for the PCR amplification are as follows: reacting at 94° C. for 5 minutes; reacting at 98° C. for 10 seconds, reacting at 55° C. for 5 seconds and reacting at 72° C. for 70 seconds, and repeating the reactions for 30 times; then reacting at 72° C. for 7 minutes; and finally, cooling to 16° C.

Further, in the step (5), the induction culture is as follows: culturing in the LB medium at 37° C. and 180 rpm for 12 hours to 16 hours, then inoculating in a fresh LB medium, and continuing to culture at 37° C. and 180 rpm until a concentration of the recombinant bacteria reaches $OD_{600}$=0.6, and after cooling to 20° C., adding isopropyl-β-D-thiogalactoside (IPTG) with a final concentration of 0.2 mM for induction for additional 16 hours.

Further, in the step (5), the step of collecting bacteria is as follows: centrifuging the bacteria after induction culture at 4° C. and 8000 rpm for 5 minutes, suspending the bacteria with physiological saline precooled to 4° C., centrifuging the bacteria again at 4° C. and 8000 rpm for 5 minutes, repeating the step of suspending with physiological saline and centrifuging twice to remove residual LB medium, and then collecting the bacteria.

Further, in the step (5), in the MOPS medium containing formamide and phosphite, a final concentration of formamide is 200 mM and a final concentration of phosphite is 1.32 mM.

Further, in the step (5), after adding the collected bacteria into the MOPS medium containing formamide and phosphite, a concentration of the bacteria $OD_{600}$ is 0.1 to 0.15.

Further, in the step (5), continuing to culture is performed after adding the IPTG with a final concentration of 0.2 mM into the MOPS medium containing formamide and phosphite at 30° C. and 180 rpm for 84 hours to 96 hours.

The MOPS medium lacks basic nutrient components $NH_4^+$ and $HPO_4^{2-}$, and is added with formamide and phosphite, and meanwhile, miscellaneous microorganisms do not have a function of decomposing formamide and oxidized phosphite to acquire a nutrient component, so that the miscellaneous microorganisms lack a nitrogen source and a phosphorus source, hence the recombinant *E. coli* acquires sufficient nutrient components to become dominant bacteria due to the function of efficiently decomposing formamide and oxidizing phosphite.

A recombinant *E. coli* expressing a fusion protein of formamidase and phosphite dehydrogenase constructed by any one of the above mentioned methods can use formamide and phosphite for growth and multiplication in the MOPS medium, and can co-express an exogenous green fluorescent protein gene to synthesize a green fluorescent protein (GFP), thus having a function of expressing an exogenous gene.

The recombinant *E. coli* expressing the fusion protein of formamidase and phosphite dehydrogenase can express the fusion protein to efficiently decompose formamide and oxidize phosphite, and can be applied in industrial fermentation of *E. coli* to synthesize an antibody or a valuable enzyme preparation, which has a very profound significance.

Compared with the current technologies, the present invention has the following advantages and beneficial effects:

(1) the recombinant *E. coli* according to the present invention can express the fusion protein of formamidase and phosphite dehydrogenase, the fusion protein can simultaneously decompose formamide to form $NH_4^+$ and oxidize phosphite to phosphate, thereby providing a nitrogen source and a phosphorus source for normal growth and multiplication of the recombinant *E. coli*, while other microorganisms cannot grow and multiply in the MOPS medium containing formamide and phosphite due to the lack of the two pathways, the problem of microbial contamination in industrial fermentation of *E. coli* is solved, the requirement on fermentation equipment is reduced, and the 1 engineered *E. coli* can perform its instinctive function of expressing the exogenous gene;

(2) the present invention solves the problem of microbial contamination of the in the fermentation process of *E. coli* through the biotechnology of genetic engineering, and the characteristic of the engineered bacteria expressing the exogenous protein cannot be lost;

(3) the recombinant *E. coli* according to the present invention can be applied to industrial fermentation of *E. coli* to synthesize an antibody or a valuable protein preparation, so that the process of enzymatically synthesizing an antibody or a valuable protein preparation is efficient, the purity of synthesized substance is high, and the problem of invasion and pollution of miscellaneous microorganisms can be prevented in the production and fermentation processes.

DESCRIPTION OF THE EMBODIMENTS

Figure 1:
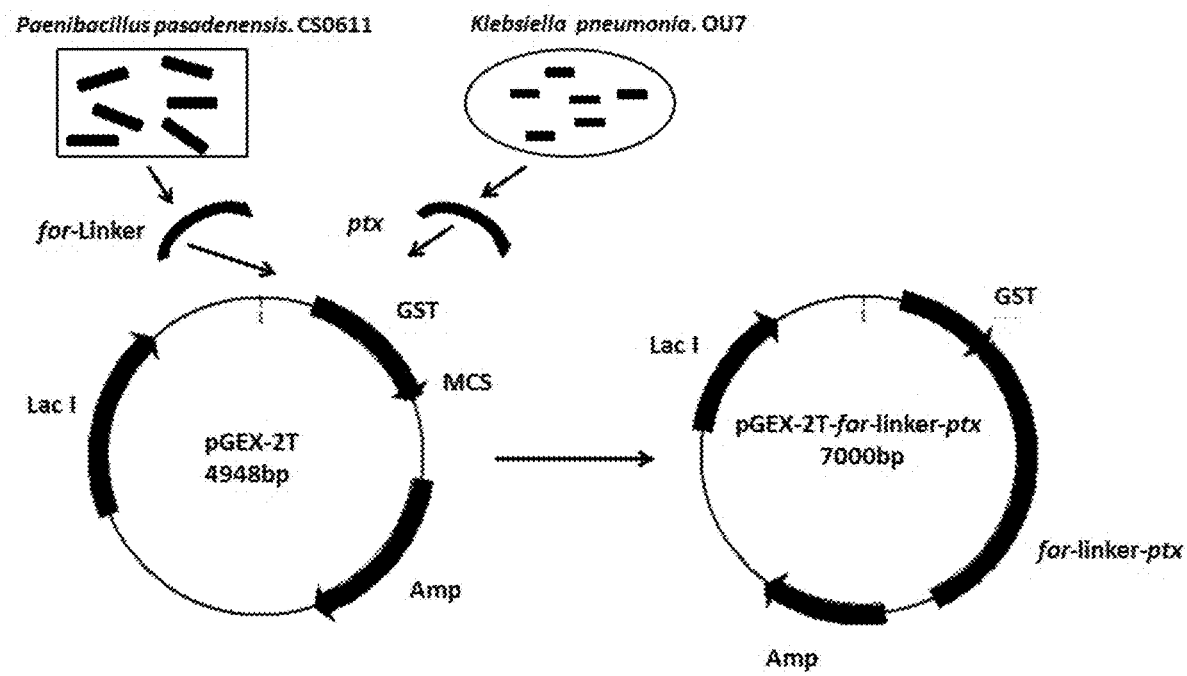
FIG. 1 is a diagram illustrating a construction process of a recombinant fusion expression plasmid pGEX-for-Linker-ptx.

In order to better understand the present invention, the technical solution of the present invention is further described hereinafter with reference to the embodiments and the accompanying drawings, but the description is only used for illustrating the present invention, and shall not and does not limit the present invention.

*Paenibacillus pasadenensis*. CS0611 used in the specific embodiments of the present invention was preserved in China Center for Type Culture Collection on Oct. 8, 2014 with a preservation number of CCTCC NO: M2014458, and a whole genome sequencing has been completed. A fragment of a formamidase gene containing a linker sequence obtained by amplification is shown in SEQ ID NO: 1, which has a fragment length of 1041 bp, contains the linker sequence, and encodes 347 amino acids.

*Klebsiella pneumonia*. OU7 used in the specific embodiments of the present invention was preserved in China Center for Type Culture Collection (Wuhan University, Luojia Mountain, Wuchang Road, Wuhan City, Hubei Province, postcode: 430072) on Aug. 24, 2017 with a preservation number of CCTCC NO: M 2017449, and the *Klebsiella pneumonia*. OU7 is obtained by culturing and self-screening by the following method. Through the sequence analysis of phosphite dehydrogenases on the NCBI database and PCR amplification, a fragment of a phosphite dehydrogenase gene is shown in SEQ ID NO: 2, which has a fragment length of 1008 bp and encodes 336 amino acids.

Embodiment 1

Acquisition of a Formamidase Gene for (Containing a Linker Sequence)

*Paenibacillus pasadenensis*. CS0611 was cultured in a LB medium at 37° C. and 180 rpm for one day; cultured bacteria were centrifuged at 4° C. and 8000 rpm for 5 minutes to collect the bacteria, the bacteria were washed twice with physiological saline to remove residual medium, and then a genome of the *Paenibacillus pasadenensis*. CS0611 was extracted according to a specific method of an OMEGA bacterial genome DNA extraction kit.

The extracted genome of the *Paenibacillus pasadenensis*. CS0611 was used as a template, A1 (5'-CGC GGATCCGATGAACGGACTGGGCGGCTTGAAC-3') of SEQ ID NO: 4 and A2 (5'-CGACCCACCACCGCCCGAGCCACCGCCACCTCGC= GCCGCGCCTCCCTTCGC-3') of SEQ ID NO: 5 were respectively used as a forward primer and a reverse primer, and a formamidase gene for-Linker was amplified by PCR.

An enzyme reagent used for PCR was PrimeSTAR® HS DNA Polymerase with GC buffer from TaKaRa Company; and a PCR reaction system and conditions were as follows:

Composition of PCR reaction liquid (25 μL)

|  | Volume |
| --- | --- |
| 2 × Prime STAR buffer | 12.5 μL |
| dNTP mixture | 2μ |
| A1 primer | 0.5 μL |
| A2 primer | 0.5 μL |
| Template | 1 μL |
| PrimeSTAR HS DNA polymerase (2.5 U/μL) | 0.25 μL |
| Deionized water | 8.25 μL |

PCR reaction conditions were as follows: reacting at 94° C. for 5 minutes; reacting at 98° C. for 10 seconds, reacting at 55° C. for 5 seconds and reacting at 72° C. for 70 seconds in sequence, and repeating the reactions for 30 times; then reacting at 72° C. for 7 minutes; and finally, cooling to 16° C.

A DNA product obtained by the PCR amplification was subjected to electrophoresis with 1 wt % agarose gel, a gel extraction kit from the OMEGA Company was used to perform gel extraction purification according to steps in the instruction, then the DNA product was sent for sequencing, and the result showed that a formamidase gene sequence containing a linker sequence with a fragment length of 1041 bp was obtained, and was named as for-Linker.

Embodiment 2

Acquisition of a Phosphite Dehydrogenase Gene Ptx

A phosphite dehydrogenase gene was derived from self-screened *Klebsiella pneumonia*. OU7, and was screened by our laboratory.

A genome of the screened *Klebsiella pneumonia*. OU7 was extracted according to a specific method of an OMEGA bacterial genome DNA extraction kit, the genome of the screened *Klebsiella pneumonia*. OU7 was used as a template, B2 (5'-TGGCTCGGGCGGTGGTGGGTC-GATGCTGCCGAAACTCGTTATA-3') of SEQ ID NO: 7 and B3 (5'-CCG*GAATTCC*GACATGCGGCAGGC-TCGGCCTTGGGC-3') of SEQ ID NO: 8 were respectively used as a forward primer and a reverse primer, and a phosphite dehydrogenase gene ptx was amplified by PCR.

An enzyme reagent used for PCR was PrimeSTAR® HS DNA Polymerase with GC buffer from TaKaRa Company; and a PCR reaction system and conditions were as follows:

Composition of PCR reaction liquid (25 μL)

|  | Volume |
| --- | --- |
| 2 × Prime STAR buffer | 12.5 μL |
| dNTP substrate | 2 μL |
| B2 primer | 0.5 μL |
| B3 primer | 0.5 μL |
| Template | 1 μL |
| PrimeSTAR HS DNA polymerase (2.5 U/μL) | 0.25 μL |
| Deionized water | 8.25 μL |

PCR reaction conditions were as follows: reacting at 94° C. for 5 minutes; reacting at 98° C. for 10 seconds, reacting at 55° C. for 5 seconds and reacting at 72° C. for 70 seconds in sequence, and repeating the reactions for 30 times; then reacting at 72° C. for 7 minutes; and finally, cooling to 16° C.

A DNA product obtained by the PCR amplification was subjected to electrophoresis with 1 wt % agarose gel, a gel extraction kit from the OMEGA Company was used to perform gel extraction purification according to steps in the instruction, then the DNA product was sent for detection and sequencing, and the result showed that a phosphite dehydrogenase gene sequence with a fragment length of 1008 bp was obtained, and was named as ptx.

Embodiment 3

Acquisition of a Fusion Gene for-Linker-Ptx by Overlapping PCR Amplification

The for-Linker and ptx fragments obtained by amplification were used as templates, A1 (5'-CGC*GGATCC*GATGAACGGACTGGGCGGCTTGAAC-3') of SEQ ID NO: 4 and B3 (5'-CCG*GAATTCC*GACATGCGGCAGGCTCGGCCTTGGGC-3') of SEQ ID NO: 8 were respectively used as a forward primer and a reverse primer, and a fusion gene for-Linker-ptx was obtained by amplification.

Amplification conditions were as follows: reacting at 94° C. for 5 minutes; reacting at 98° C. for 10 seconds, reacting at 55° C. for 5 seconds and reacting at 72° C. for 70 seconds in sequence, and repeating the reactions for 30 times; then reacting at 72° C. for 7 minutes; and finally, cooling to 16° C.

Embodiment 4

Construction of a Recombinant *E. coli* BL21(DE3) (pGEX-for-Linker-Ptx)

Double digestion was performed on the fusion gene for-Linker-ptx obtained in the embodiment 3 and a plasmid pGEX-2T respectively with BamH I and EcoR I, an underlined and italic part of a forward primer was a restriction enzyme cutting site of BamH I, an underlined and italic part of a reverse primer was a restriction enzyme cutting site of EcoR I, and digestion conditions were as follows: digesting at 37° C. for 120 minutes;

Digestion system:

|  | Fusion gene (μL) | Plasmid (μL) |
| --- | --- | --- |
| ddH$_2$O | 5 | 0 |
| 10 × buffer | 3 | 2 |
| Fragment/plasmid | 20 | 16 |
| BamH I + EcoR I | 1 + 1 | 1 + 1 |
| Total volume | 30 | 20 |

Gel extraction purification was performed on a digested product respectively, and a extraction method and steps referred to a gel extraction kit from the OMEGA Company; the digested product was subjected to electrophoresis with 1 wt % agarose gel after extraction, and a extraction rate was detected; and then a extracted target fragment was ligated to a plasmid, T4 DNA Ligase from Thermo Fisher SCIENTIFIC Company was used as a ligation kit, and a ligation system was as follows:

| DNA fragment | 6 μL |
| --- | --- |
| Plasmid | 9 μL |
| 10 × T4 buffer | 2 μL |
| T4 DNA ligase | 1 Weiss U |

-continued

| Deionized water | 2 µL |
| Total volume | 20 µL |

A molar ratio of the fusion gene to the pGEX-2T plasmid was 5:1.

A ligation product was transformed into an E. coli DH5α, and transformation steps were as follows: 10 µL of the ligation product was mixed with 100 µL of competent cells of the E. coli DH5α, the mixture was placed into ice bath for 30 minutes, heat shock at 42° C. for 90 seconds, and then ice bath for 2 minutes, then 890 µL of LB medium was added, and after shaking culture at 37° C. and 180 rpm for 1 hour, the mixture was centrifuged at 4000 rpm for 5 minutes to collect bacteria; 890 µL of supernatant medium was taken, the bacteria at a bottom of a tube were resuspended, evenly coated on a LB solid plate containing ampicillin (containing 100 µg/mL ampicillin sodium), and cultured at 37° C. for 16 hours; and after transformants grew on the plate, the transformants were selected for PCR verification and sent for detection and sequencing, and ORF search was performed on the sequencing result using DNAssist software.

The result shows that the obtained fusion gene sequence (for-Linker-ptx) has been correctly inserted into a multiple cloning site of pGEX-2T, and the pGEX-for-Linker-ptx plasmid has been successfully obtained and transformed into E. coli BL21(DE3) competent cell to obtain a recombinant E. coli BL21(DE3)(pGEX-for-Linker-ptx).

A construction process of the recombinant E. coli BL21 (DE3)(pGEX-for-Linker-ptx) assimilating and metabolizing formamide and phosphite to become dominant engineered bacteria in a medium is shown in FIG. 1. Due to insertion of a fusion gene (a formamidase gene+Linker+a phosphite dehydrogenase gene) into the E. coli BL21(DE3)(pGEX-for-Linker-ptx), the modified E. coli BL21(DE3)(pGEX-for-Linker-ptx) not only can decompose formamide into $NH_4^+$ but also can oxidize phosphite to phosphate, thus providing a nitrogen source and a phosphorus source for the growth of the E. coli BL21(DE3)(pGEX-for-Linker-ptx), while other miscellaneous microorganisms cannot grow due to the lack of the two pathways.

Embodiment 5

Growth of an E. coli BL21(DE3)(pGEX-for-Linker-Ptx) in a Specific MOPS Medium

Induction culture was performed on the obtained recombinant expression strain E. coli BL21(DE3)(pGEX-for-Linker-ptx), and a specific process was as follows:

E. coli BL21(DE3)(pGEX-for-Linker-ptx) was inoculated to 30 mL of LB medium according to a volume ratio of 1:100, and cultured at 37° C. and 180 rpm overnight for 16 hours; induction culture was performed, 1 mL of recombinant E. coli cultured overnight was inoculated to 100 mL of fresh LB medium, and cultured at 37° C. and 180 rpm until a concentration of recombinant bacteria reached $OD_{600}$=0.6, and after cooling to 20° C., IPTG with a final concentration of 0.2 mM was added for induction for 16 hours, and bacteria were collected by centrifuging at 4° C. and 8000 rpm for 5 minutes.

The collected bacteria were suspended with physiological saline (precooled at 4° C.), and centrifuged at 4° C. and 8000 rpm for 5 minutes to collect bacteria, and this step was repeated twice to remove residual LB medium; the bacteria were added to a basic MOPS medium containing formamide (200 mM) and phosphite (1.32 mM) to make $OD_{600}$ of the bacteria be 0.1, IPTG with a final concentration of 0.2 mM was added, and the recombinant E. coli was continued to be cultured at 30° C. and 180 rpm.

Figure 2:
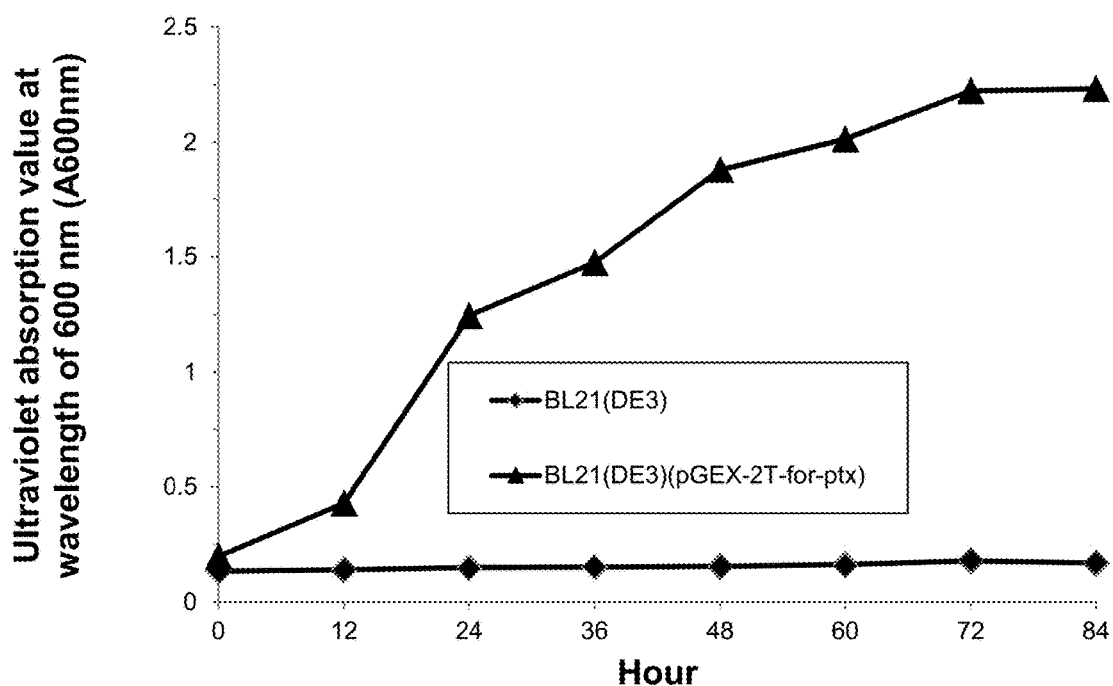
FIG. 2 is a growth curve graph of a recombinant *Escherichia coli* BL21 (DE3)(pGEX-for-Linker-ptx) in a MOPS medium.

The growth of the recombinant E. coli in the MOPS medium is observed, a growth curve graph of the recombinant E. coli BL21(DE3)(pGEX-for-Linker-ptx) in the MOPS medium containing formamide (200 mM) and phosphite (1.32 mM) is shown in FIG. 2. It can be seen from FIG. 2 that the recombinant E. coli BL21(DE3)(pGEX-for-Linker-ptx) can grow in this medium, a concentration of bacteria reaches a maximum value after the third day, and A600 is 2.223, while a control strain E. coli BL21(DE3) basically does not grow in the MOPS medium.

Figure 3:
FIG. 3 is a photofluorogram of the recombinant *Escherichia coli* BL21 (DE3)(pGEX-for-Linker-ptx) expressing a green fluorescent protein (GFP) in the MOPS medium.

In order to verify an express ability of the recombinant E. coli BL21(DE3)(pGEX-for-Linker-ptx) to synthesize exogenous gene in the MOPS medium, a green fluorescent protein (GFP) gene was used to verify an ability of the recombinant E. coli to express an exogenous gene. The pET-28a-GFP plasmid was transformed into E. coli BL21 (DE3)(pGEX-for-Linker-ptx) to form the recombinant E. coli, which was named as E. coli BL21(DE3)(pGEX-for-Linker-ptx+pET-28a-GFP), and the obtained recombinant E. coli was induced to express GFP in the MOPS medium containing formamide and phosphite. Then, the cultured and fermented recombinant E. coli was observed with a fluorescence inversion microscope with an excitation wavelength of 488 nm and an emission wavelength of 507 nm. It can be seen from FIG. 3 that the recombinant E. coli can grow normally in the MOPS medium and can express an exogenous green fluorescent protein gene.

The instant application contains a Sequencing Listing which has been submitted electronically in ASCII text file and is hereby incorporated by reference in its entirety. Said ASCII text file, created on Jan. 7, 2023, is named 096868-US-sequence listing ST25 and is 7,681 bytes in size.

What is claimed is:

1. A method for constructing a recombinant *Escherichia coli* expression stain which expresses a fusion of a formamidase and a phosphite dehydrogenase, comprising the following steps:
   (1) amplifying a formamidase gene fragment with a linker sequence by polymerase chain reaction using a first pair of primers and a genome of *Paenibacillus pasadenensis* CS0611 as a template to clone a formamidase gene with a linker sequence (for-Linker) of 1041 bp, wherein the first pair of primers comprises a forward primer (primer A1) and a reverse (primer A2), wherein the nucleotide sequence of primer A1 is SEQ ID NO: 4 and the nucleotide sequence of primer A2 is SEQ ID NO: 5, wherein the *Paenibacillus pasadenensis* CS0611 has China Center for Type Culture Collection (CCTCC) deposit number M 2014458;
   (2) ligating the for-Linker into a vector to obtain a recombinant vector comprising the for-Linker (vector-for) and transforming *E. coli* DH5α competent cells with the recombinant vector for to obtain a recombinant *E. coli* DH5α containing the recombinant vector-for;
   (3) amplifying the for-Linker in the recombinant vector-for by PCR using a second pair of primers and the vector for as a template, wherein the second pair of primers comprises the forward primer A1 and a reverse primer (primer B1), wherein the nucleotide sequence of primer B1 is SEQ ID NO: 6;
   (4) amplifying a phosphite dehydrogenase gene fragment by PCR using a third pair of primers and a genome of *Klebsiella pneumoniae* OU7 as a template to clone a phosphite dehydrogenase gene (ptx) of 1008 bp, wherein the third pair of primers comprises a forward primer (primer B2) and a reverse primer (primer B3), wherein the nucleotide sequence of primer B2 is SEQ ID NO: 7 and the nucleotide sequence of primer B3 is SEQ ID NO: 8, wherein the *Klebsiella pneumoniae* OU7 has CCTCC deposit number M 2017449;
   (5) generating a fusion gene (for-Linker-ptx) by overlapping PCR amplification using a fourth pair of primers and the amplified for-Linker of step (3) and the amplified ptx of step (4) as templates, wherein the fourth pair of primers comprises the forward primer A1 and the reverse primer B3;
   (6) digesting the for-Linker-ptx fusion gene with BamHI and EcoRI and ligating the digested for-Linker-ptx fusion gene into a pGEX-2T expression plasmid digested with BamHI and EcoRI to obtain a recombinant plasmid comprising the for-Linker-ptx fusion gene (pGEX-for-Linker-ptx), and transforming *E. coli* DH5α competent cells with the recombinant plasmid pGEX-for-Linker-ptx to obtain a recombinant *E. coli* DH5α comprising the recombinant plasmid pGEX-for-Linker-ptx;
   (7) extracting the recombinant plasmid pGEX-for-Linker-ptx from the recombinant *E. coli* DH5α comprising the recombinant plasmid pGEX-for-Linker-ptx and transforming *E. coli* BL21(DE3) competent cells with the recombinant plasmid pGEX-for-Linker-ptx to obtain a recombinant *E. coli* expression strain; and
   (8) inoculating a LB medium with the recombinant *E. coli* expression strain, inducing expression of the for-Linker-ptx fusion gene, collecting the recombinant *E. coli* expression strain, adding the recombinant *E. coli* expression strain to a MOPS medium comprising formamide and phosphite, and culturing the recombinant *E. coli* expression strain in the MOPS medium comprising formamide and phosphite.

2. The method of claim 1, wherein in step (3), the amplified for-Linker comprises the nucleotide sequence of SEQ ID NO: 1.

3. The method of claim 1, wherein in step (4), the amplified ptx comprises the nucleotide sequence of SEQ ID NO: 2.

4. The method of claim 1, wherein in step (5), the for-Linker-ptx fusion gene comprises the nucleotide sequence of SEQ ID NO: 3.

5. The method of claim 1, wherein in steps (1), (3) and (4), conditions for the PCR amplification comprise reacting at 94° C. for 5 minutes; reacting at 98° C. for 10 seconds, reacting at 55° C. for 5 seconds and reacting at 72° C. for 70 seconds, and repeating reactions for 30 times; then reacting at 72° C. for 7 minutes; and finally, cooling to 16° C.

6. The method of claim 1, wherein in step (8), inducing expression of the for-Linker-ptx fusion gene comprises culturing in a LB medium at 37° C. and 180 rpm for 12 hours to 16 hours, then inoculating in a fresh LB medium, and continuing to culture at 37° C. and 180 rpm until $OD_{600}$ of the recombinant *E. coli* expression stain in the culture reaches 0.6, and after cooling to 20° C., adding isopropyl-3-D-thiogalactoside (IPTG) with a final concentration of 0.2 mM for induction for 16 hours.

7. The method of claim 1, wherein in step (8), collecting the recombinant *E. coli* expression strain comprises centrifuging the recombinant *E. coli* expression strain at 4° C. and 8000 rpm for 5 minutes, suspending the recombinant *E. coli* expression strain with physiological saline precooled to 4° C., centrifuging again at 4° C. and 8000 rpm for 5 minutes, repeating the suspending with physiological saline and centrifuging twice, and then collecting the recombinant *E. coli* expression strain; and wherein in the MOPS medium comprising formamide and phosphite, a final concentration of the formamide is 200 mM and a final concentration of the phosphite is 1.32 mM.

8. The method of claim 1, wherein in step (8), after adding the collected recombinant *E. coli* expression strain into the MOPS medium comprising formamide and phosphite, the $OD_{600}$ of the recombinant *E. coli* expression strain in the medium is 0.1 to 0.15, inducing expression of the for-Linker-ptx fusion gene with IPTG at a final concentration of 0.2 mM, and culturing the recombinant *E. coli* expression strain in the MOPS medium containing formamide and phosphite at 30° C. and 180 rpm for 84 hours to 96 hours.

* * * * *

SEQUENCE LISTING

```
<160> NUMBER OF SEQ ID NOS: 11

<210> SEQ ID NO 1
<211> LENGTH: 1041
<212> TYPE: DNA
<213> ORGANISM: Paenibacillus pasadenensis CS0611

<400> SEQUENCE: 1
atgaacggac tgggcggctt gaacaaatcg ccggacggcg tcgtcatcgg cctcgcgcag      60
ctgcagctgc cggccgtcga gacgccggag cagctggcgg cgcaggcgag gcgcatcgcg     120
```

```
gagatgacgg ccaaggcgcg aagggctcg cgctcgatgg atctgatcgt atttcccgaa      180
tattcgctgc atggcctatc gatgaatacc gatccggcgc tcatgtgccg ggtcgacggg      240
ccggaggtcg agctgtggcg ggaggcctgc cgcgagcatc gcatctgggg ctgcttcagc      300
atcatggagc tcaatccgga cggcaatccg tacaacacgg gctcatcat cgacgacgaa       360 ggcggaatcc ggctgaagta ccgcaagctg catccgtggg tgccggtgga gccgtgggag      420
ccgggcgatc tcggcatccc gatgtgcgac gggccgaacg gcagccggtt ggcgctcgtc      480
atctgccatg acggcatgtt cccggaaatg gcgcgcgaat gcgcctatct cggtgcggac      540
atcatgctgc gcacggccgg ctatacggct ccgatccgcc atgcatggca ggtgacgaac      600
caggcgcacg ccttttgcaa cctgatgtac accgcctcgg tctgcctgag tggcagcgac      660
ggcgtcttcg actcgatggg cgaggcgatg atcgtcggct tcgacggcat gacgctcgtc      720
cacggcggcg gacggcccga cgagatcgtg gccggcgagg tgcggccgtc gctcgtccgc      780
gaggcgcgcc gcatctgggg cgtggagaac aacctgtacc agctcggcca tcgcggctac      840
gtcgcggtgc agggcggcgc aggcgactgt ccgtacacct acatgcatga tctcgccgcc      900
ggccgctacc ggctgccttg ggaggatgag gtgctcatca aggacggcac gagcgagggg      960
ttcccgccgc cggagcggcg atatggcgga gcgaagggag gcgcggcgcg aggtggcggt     1020
ggctcgggcg gtggtgggtc g                                              1041

<210> SEQ ID NO 2
<211> LENGTH: 1008
<212> TYPE: DNA
<213> ORGANISM: Klebsiella pneumonia OU7

<400> SEQUENCE: 2
atgctgccga aactcgttat aactcaccga gtacacgatg agatcctgca actgctggcg       60
ccacattgcg agctggtgac caaccagacc gacagcacgc tgacgcgcga ggaaattctg      120
cgccgctgtc gcgatgctca ggcgatgatg gcgttcatgc ccgatcgggt cgatgcagac      180
tttcttcaag cctgccctga gctgcgtgta gtcggctgcg cgctcaaggg cttcgacaat      240
ttcgatgtgg acgcctgtac tgcccgcggg gtctggctga ccttcgtgcc tgatctgttg      300
acggtcccga ctgccgagct ggcgatcgga ctggcggtgg ggctggggcg gcatctgcgg      360
gcagcagatg cgttcgtccg ctctggcgag ttccagggct ggcaaccaca gttctacggc      420
acggggctgg ataacgctac ggtcggcatc cttggcatgg gcgccatcgg actggccatg      480
gctgagcgct tgcagggatg gggcgcgacc ctgcagtacc acgaggcgaa ggctctggat      540
acacaaaccg agcaacggct cggcctgcgc caggtggcgt gcagcgaact cttcgccagc      600
tcggacttca tcctgctggc gcttcccttg aatgccgata cccagcatct ggtcaacgcc      660
gagctgcttg ccctcgtacg gccgggcgct ctgcttgtaa accctgtcg tggttcggta      720 gtggatgaag ccgccgtgct cgcggcgctt gagcgaggcc agctcggcgg gtatgcggcg      780
gatgtattcg aaatggaaga ctgggctcgc gcggaccggc cgcggctgat cgatcctgcg      840
ctgctcgcgc atccgaatac gctgttcact ccgcacatag ggtcggcagt gcgcgcggtg      900
cgcctggaga ttgaacgttg tgcagcgcag aacatcatcc aggtattggc aggtgcgcgc      960
ccaatcaacg ctgcgaaccg tctgcccaag gccgagcctg ccgcatgt                  1008

<210> SEQ ID NO 3
<211> LENGTH: 2049
<212> TYPE: DNA
<213> ORGANISM: Artificial Sequence
```

<220> FEATURE:
<223> OTHER INFORMATION: fusion protein of formamidase, linker and phosphite dehydrogenase

<400> SEQUENCE: 3

| | | | | | |
|---|---|---|---|---|---|
| atgaacggac | tgggcggctt | gaacaaatcg | ccggacggcg | tcgtcatcgg | cctcgcgcag | 60 |
| ctgcagctgc | cggccgtcga | gacgccggag | cagctggcgg | cgcaggcgag | gcgcatcgcg | 120 |
| gagatgacgg | ccaaggcgcg | gaagggctcg | cgctcgatgg | atctgatcgt | atttcccgaa | 180 |
| tattcgctgc | atggcctatc | gatgaatacc | gatccggcgc | tcatgtgccg | ggtcgacggg | 240 |
| ccggaggtcg | agctgtggcg | ggaggcctgc | cgcgagcatc | gcatctgggg | ctgcttcagc | 300 |
| atcatggagc | tcaatccgga | cggcaatccg | tacaacacgg | ggctcatcat | cgacgacgaa | 360 |
| ggcggaatcc | ggctgaagta | ccgcaagctg | catccgtggg | tgccggtgga | gccgtgggag | 420 |
| ccgggcgatc | tcggcatccc | gatgtgcgac | gggccgaacg | gcagccggtt | ggcgctcgtc | 480 |
| atctgccatg | acggcatgtt | cccggaaatg | gcgcgcgaat | gcgcctatct | cggtgcggac | 540 |
| atcatgctgc | gcacggccgg | ctatacggct | ccgatccgcc | atgcatggca | ggtgacgaac | 600 |
| caggcgcacg | ccttttgcaa | cctgatgtac | accgcctcgg | tctgcctgag | tggcagcgac | 660 |
| ggcgtcttcg | actcgatggg | cgaggcgatg | atcgtcggct | tcgacggcat | gacgctcgtc | 720 |
| cacggcggcg | gacggcccga | cgagatcgtg | gccggcgagg | tgcggccgtc | gctcgtccgc | 780 |
| gaggcgcgcc | gcatctgggg | cgtggagaac | aacctgtacc | agctcggcca | tcgcggctac | 840 |
| gtcgcggtgc | agggcggcgc | aggcgactgt | ccgtacacct | acatgcatga | tctcgccgcc | 900 |
| ggccgctacc | ggctgccttg | ggaggatgag | gtgctcatca | aggacggcac | gagcgagggg | 960 |
| ttcccgccgc | cggagcggcg | atatggcgga | gcgaagggag | gcgcggcgcg | aggtggcggt | 1020 |
| ggctcgggcg | tggtgggtc | gatgctgccg | aaactcgtta | taactcaccg | agtacacgat | 1080 |
| gagatcctgc | aactgctggc | gccacattgc | gagctggtga | ccaaccagac | cgacagcacg | 1140 |
| ctgacgcgcg | aggaaattct | cgccgctgt | cgcgatgctc | aggcgatgat | ggcgttcatg | 1200 |
| cccgatcggg | tcgatgcaga | ctttcttcaa | gcctgccctg | agctgcgtgt | agtcggctgc | 1260 |
| gcgctcaagg | gcttcgacaa | tttcgatgtg | acgcctgta | ctgcccgcgg | ggtctggctg | 1320 |
| accttcgtgc | ctgatctgtt | gacggtcccg | actgccgagc | tggcgatcgg | actggcggtg | 1380 |
| gggctggggc | ggcatctgcg | ggcagcagat | gcgttcgtcc | gctctggcga | gttccagggc | 1440 |
| tggcaaccac | agttctacgg | cacggggctg | gataacgcta | cggtcggcat | ccttggcatg | 1500 |
| ggcgccatcg | gactggccat | ggctgagcgc | ttgcagggat | ggggcgcgac | cctgcagtac | 1560 |
| cacgaggcga | aggctctgga | tacacaaacc | gagcaacggc | tcggcctgcg | ccaggtggcg | 1620 |
| tgcagcgaac | tcttcgccag | ctcggacttc | atcctgctgg | cgcttccctt | gaatgccgat | 1680 |
| acccagcatc | tggtcaacgc | cgagctgctt | gccctcgtac | ggccgggcgc | tctgcttgta | 1740 |
| aaccctgtc | gtggttcggt | agtggatgaa | gccgccgtgc | tcgcggcgct | tgagcgaggc | 1800 |
| cagctcggcg | ggtatgcggc | ggatgtattc | gaaatggaag | actgggctcg | cgcggaccgg | 1860 |
| ccgcggctga | tcgatcctgc | gctgctcgcg | catccgaata | cgctgttcac | tccgcacata | 1920 |
| gggtcggcag | tgcgcgcggt | gcgcctggag | attgaacgtt | gtgcagcgca | gaacatcatc | 1980 |
| caggtattgg | caggtgcgcg | cccaatcaac | gctgcgaacc | gtctgcccaa | ggccgagcct | 2040 |
| gccgcatgt | | | | | | 2049 |

<210> SEQ ID NO 4
<211> LENGTH: 34

```
<212> TYPE: DNA
<213> ORGANISM: Artificial Sequence
<220> FEATURE:
<223> OTHER INFORMATION: Forward primer A1

<400> SEQUENCE: 4
cgcggatccg atgaacggac tgggcggctt gaac                              34

<210> SEQ ID NO 5
<211> LENGTH: 51
<212> TYPE: DNA
<213> ORGANISM: Artificial Sequence
<220> FEATURE:
<223> OTHER INFORMATION: Reverse primer A2

<400> SEQUENCE: 5
cgacccacca ccgcccgagc caccgccacc tcgcgccgcg cctcccttcg c           51

<210> SEQ ID NO 6
<211> LENGTH: 43
<212> TYPE: DNA
<213> ORGANISM: Artificial Sequence
<220> FEATURE:
<223> OTHER INFORMATION: Reverse primer B1

<400> SEQUENCE: 6
tataacgagt tcggcagca tcgacccacc accgcccgag cca                    43

<210> SEQ ID NO 7
<211> LENGTH: 43
<212> TYPE: DNA
<213> ORGANISM: Artificial Sequence
<220> FEATURE:
<223> OTHER INFORMATION: Forward primer B2

<400> SEQUENCE: 7
tggctcgggc ggtggtgggt cgatgctgcc gaaactcgtt ata                   43

<210> SEQ ID NO 8
<211> LENGTH: 36
<212> TYPE: DNA
<213> ORGANISM: Artificial Sequence
<220> FEATURE:
<223> OTHER INFORMATION: Reverse primer B3

<400> SEQUENCE: 8
ccggaattcc gacatgcggc aggctcggcc ttgggc                            36

<210> SEQ ID NO 9
<211> LENGTH: 30
<212> TYPE: DNA
<213> ORGANISM: Artificial Sequence
<220> FEATURE:
<223> OTHER INFORMATION: DNA Linker

<400> SEQUENCE: 9
ggtggcggtg gctcgggcgg tggtgggtcg                                   30

<210> SEQ ID NO 10
<211> LENGTH: 30
<212> TYPE: DNA
<213> ORGANISM: Artificial Sequence
<220> FEATURE:
<223> OTHER INFORMATION: linker sequence

<400> SEQUENCE: 10
```

```
cgacccacca ccgcccgagc caccgccacc                                        30
```

```
<210> SEQ ID NO 11
<211> LENGTH: 22
<212> TYPE: DNA
<213> ORGANISM: Artificial Sequence
<220> FEATURE:
<223> OTHER INFORMATION: partial DNA of the linker

<400> SEQUENCE: 11
tggctcgggc ggtggtgggt cg                                                22
```